United States Patent [19]
Effland et al.

[11] Patent Number: 5,095,019
[45] Date of Patent: Mar. 10, 1992

[54] 4-SUBSTITUTED DIHYDROPYRIDO(4,3-D)PYRIMIDINES AS ANALGESICS AND TOPICAL ANTIINFLAMMATORY AGENTS FOR THE TREATMENT OF SKIN DISORDERS

[75] Inventors: Richard C. Effland; Joseph T. Klein, both of Bridgewater, N.J.

[73] Assignee: Hoechst-Roussel Pharmaceuticals Inc., Somerville, N.J.

[21] Appl. No.: 740,171

[22] Filed: Aug. 5, 1991

Related U.S. Application Data

[62] Division of Ser. No. 573,414, Aug. 27, 1990, Pat. No. 5,059,602.

[51] Int. Cl.$^5$ .......................................... A61K 31/505
[52] U.S. Cl. ................................. 514/258; 544/279; 546/309; 546/311
[58] Field of Search ............................. 514/258

[56] References Cited

U.S. PATENT DOCUMENTS 4,614,743  9/1986  Chipkin et al. .................. 514/258
4,950,648  8/1990  Raddatz et al. .................. 514/258
5,059,602  10/1991  Effland et al. .................. 514/258

Primary Examiner—Robert T. Bond
Assistant Examiner—E. Bernhardt
Attorney, Agent, or Firm—Tatsuya Ikeda

[57] ABSTRACT

There are described compounds of the formula

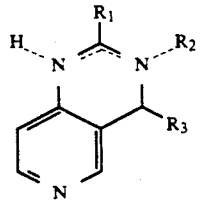

where
  $R_1$ is hydrogen, loweralkyl, arylloweralkyl or aryl;
  $R_2$ when present is hydrogen, loweralkyl, arylloweralkyl; and
  $R_3$ is hydrogen, loweralkyl, cycloalkyl or aryl;
which compounds are useful as analgesics and topical antiinflammatory agents for the treatment of skin disorders.

3 Claims, No Drawings

4-SUBSTITUTED DIHYDROPYRIDO(4,3-D)PYRIMIDINES AS ANALGESICS AND TOPICAL ANTIINFLAMMATORY AGENTS FOR THE TREATMENT OF SKIN DISORDERS

This is a division of a prior application, Ser. No. 573,414, filed Aug. 27, 1990, now U.S. Pat. No. 5,059,602.

The present invention relates to compounds of Formula I,

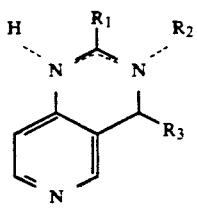

where
$R_1$ is hydrogen, loweralkyl, arylloweralkyl or aryl;
$R_2$ when present is hydrogen, loweralkyl, arylloweralkyl; and
$R_3$ is hydrogen, loweralkyl, cycloalkyl or aryl;
which compounds are useful as analgesics and topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

The dotted lines present in Formula I signify optional bonds. Specifically, Formula I covers two groups of compounds depicted by Formula II and Formula III below.

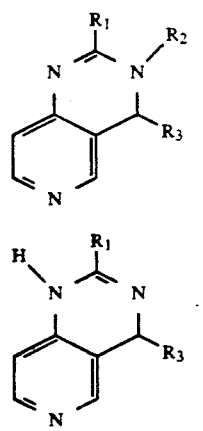

Throughout the specification and the appended claims, a given chemical formula or name shall encompass all stereo isomers and tautomeric isomers where such isomers exist.

Unless otherwise stated or indicated, the following definitions shall apply throughout the specification and the appended claims.

The term loweralkyl shall mean a straight or branched alkyl group having from 1 to 6 carbon atoms.

Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

The compounds of this invention are prepared by utilizing one or more of the synthetic steps described below.

Throughout the description of the synthetic steps, the notations $R_1$, $R_2$ and $R_3$ shall have the respective meanings given above unless otherwise stated or indicated.

STEP A

The compound of Formula IV is allowed to react with a Grignard reagent of the formula $R_3'$-Mg-Br where $R_3'$ is loweralkyl, cycloalkyl or aryl in a routine manner known to the art to afford a compound of Formula V. The starting compound of Formula IV is disclosed in Turner, J. Org. Chem. 48 3401 (1983).

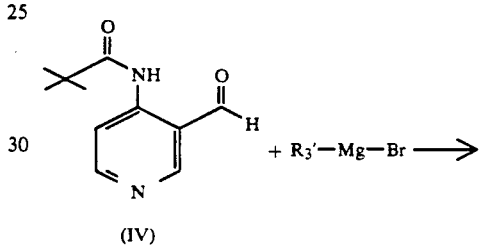

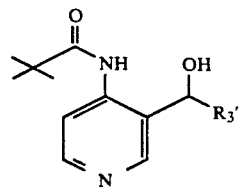

STEP B

Compound V is allowed to react with pyridinium dichromate to afford a compound of Formula VI. This reaction is typically conducted in a suitable solvent such as dimethylformamide at a temperature of about 0° to 150° C.

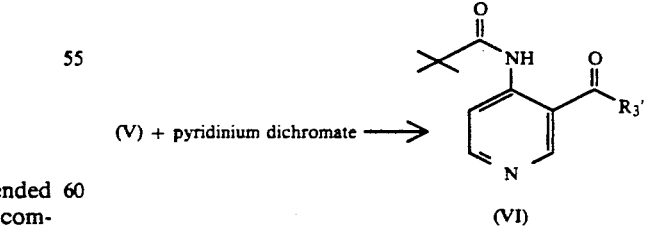

STEP C

A compound of Formula VII (which is obtained from STEP B when $R_3$ is loweralkyl, cycloalkyl or aryl; and which is the same as Compound IV when $R_3$ is hydrogen) is hydrolyzed to afford a compound of Formula VIII. This hydrolysis is typically conducted in the presence of aqueous NaOH dissolved in a suitable solvent such as loweralkanol at a temperature of about 20° to 120° C.

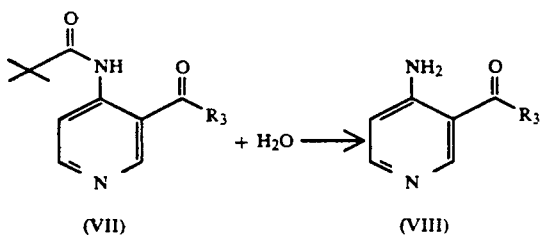

STEP D

Compound VIII is allowed to react with hydroxylamine hydrochloride to afford a compound of Formula IX. This reaction is typically conducted in the presence of a suitable solvent such as pyridine at a temperature of about 20° to 115° C.

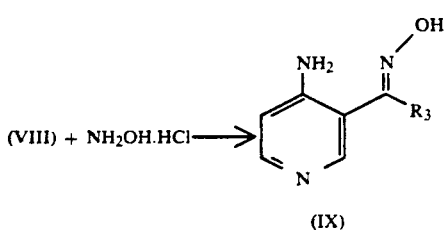

STEP E

Compound IX is hydrogenated with the aid of a Raney alloy in a routine manner known to the art to afford a compound of Formula X. As an example of Raney alloy suitable for this reaction, one can cite 50:50 Al/Ni alloy.

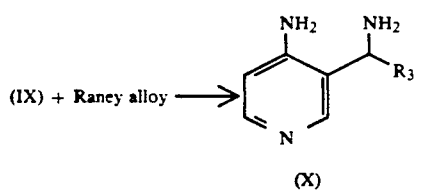

STEP F

Compound X is allowed to react with an ortho ester of Formula XI to afford Compound III. This reaction is typically conducted in a suitable solvent such as glacial acetic acid at a temperature of about 20° to 120° C.

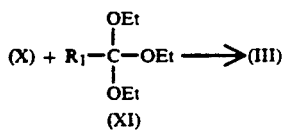

STEP G

Compound VII is allowed to react with a primary amine of the formula

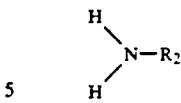

to afford a corresponding imine and thereafter the resultant imine is reduced with sodium borohydride to afford a compound of Formula XII. Said imine formation is typically conducted with the aid of a suitable acidic catalyst such as p-toluenesulfonic acid and a suitable solvent such as xylene at a temperature of about 80° to 140° C. The reduction of the imine with sodium borohydride is typically conducted in a suitable medium such as a mixture of isopropanol and methanol at a temperature of about 20° to 80° C.

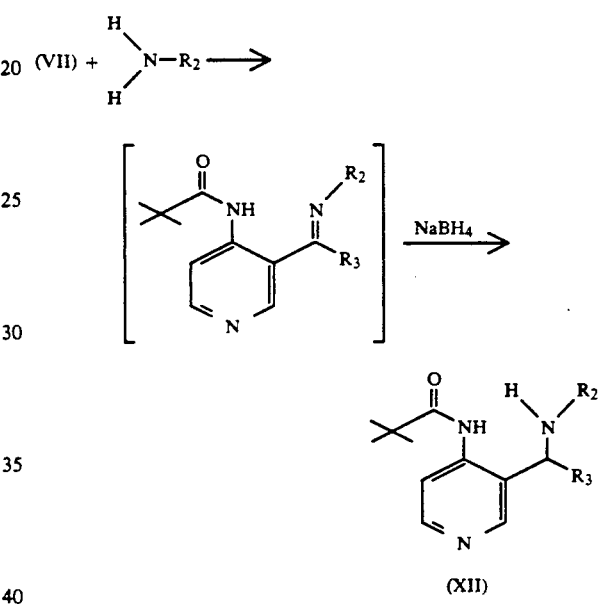

STEP H

Compound XII is hydrolyzed in substantially the same manner as in STEP C to afford a compound of Formula XIII.

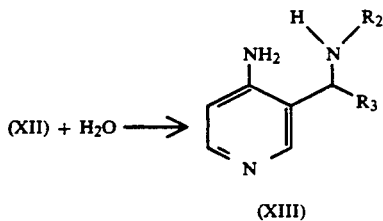

STEP I

Compound XIII is allowed to react with an ortho ester of Formula XI in substantially the same manner as in STEP F to afford Compound II.

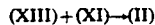

Compounds of Formula I according to this invention are useful as topical agents for the treatment of various skin disorders such as those mentioned earlier. The dermatological activities of the compounds of this invention were ascertained with reference to the following methods.

DERMATOLOGICAL TEST METHODS

Phospholipase A₂-induced Paw Edema (PIPE)

The ability of compounds to prevent naja naja (snake venom) phospholipase A₂-induced paw edema in male Wistar rats (100-125 g) was measured. $PLA_2$ (3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone $ED_{50}=0.46M$). See Giessler, A. J. et al., *Agents and Actions*, Vol. 10, Trends in Inflammation Research (1981), p. 195.

In Vitro Phospholipase A₂ Assay (PLA₂)

The ability of a compound to modulate $PLA_2$ activity (cleavage of $^{14}C$-dipalmitoyl phosphatidylcholine at the 2-position to $^{14}C$-palmitic acid) was quantitated in this assay. The reaction mixture contained Tris buffer (25 mM), pH 8.0, calcium chloride (2.0 mM), bovine serum albumin (0.5 mg), dipalmitoyl phosphatidylcholine ($8 \times 10^{-5}M$), ($^{14}C$-palmitoyl)dipalmitoyl phosphatidylcholine ($6 \times 10^3$ cpm), porcine pancreatic $PLA_2$ (3.2 units) and the test compound. The reaction was run at 37° C. in a shaking incubator. The reaction was quenched and an internal standard was added in order to determine sample recovery. The samples were loaded onto $C_{18}$ columns, eluted with ethanol, and the radioactivity was then measured. (standard: quinacrine $IC_{50}=3.5 \times 10^{-4}M$). See Feyen, J. H. M., et al., Journal of Chromatography 259 (1983), pp. 338-340.

Arachidonic Acid-Induced Ear Edema (AAEE)

The purpose of this assay was to determine the ability of a topically-applied compound to prevent mouse ear edema induced by topical application of arachidonic acid. Female Swiss Webster mice topically received vehicle or test compound (1.0 mg/ear) on both ears (10 μl on outer and inner ears). After 30 minutes, the right ear of all groups received arachidonic acid (4 mg/ear) and the left ear received vehicle alone. After an additional 1 hour, the mice were sacrificed and an ear punch (4 mm) was taken from each ear. The difference in right and left ear punch weights for each animal was determined to assess activity. (Standard: indomethacin $ED_{50}=1.5$ mg/ear). See Young, J. M. et al., *Invest. Dermatol.*, 80, (1983), pp 48-52.

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J. M. et al., *J. Invest. Dermatol.*, 80 (1983), pp. 48-52.

Dermatological activities for some of the compounds of this invention are presented in Table 1.

TABLE 1

| Compound | PIPE* (0.1M) | PLA₂* (0.01M) | AAEE (1.0 mg) | TPAEE (10 μg) |
|---|---|---|---|---|
| N-[3-[(butylamino)methyl]-4-pyridinyl]-2,2-dimethylpropanamide dihydrochloride | | | −45% | |
| α-methyl-α-[4-(2,2-dimethylpropionamido)-3-pyridinyl]-methanol | | | | −46% |
| N-[3-[1-(phenylmethylamino)ethyl]-4-pyridinyl]-2,2-dimethylpropionamide dihydrochloride | | −74% | −44% | |
| 4-amino-α-methyl-N-(phenylmethyl)-3-pyridinemethanamine | | | | −45% |
| 3-[(phenylmethylamino)methyl]-4-pyridinamine dihydrochloride | −51% | −79% | | |
| α-cyclohexyl-α-[4-(2,2-dimethylpropionamido)-3-pyridinyl]-methanol | −35% | | −52% | −55% |
| (4-amino-3-pyridinyl)-cyclohexylmethanone hydrochloride | | −82% | | −53% |
| (4-amino-3-pyridinyl)-cyclohexylmethanone oxime hydrochloride | | −99% | | −34% |
| (4-amino-3-pyridinyl)-cyclohexylmethanamine dihydrochloride | −68% | −72% | −28% | −36% |
| (4-amino-3-pyridinyl)-phenylmethanone oxime hydrochloride | | | | −32% |
| (4-amino-3-pyridinyl)-benzenemethanamine dihydrochloride | −66% | | | |
| 4-cyclohexyl-1,4-dihydropyrido[4,3-d]-pyrimidine dihydrochloride | −44% | | | |
| 3,4-dihydro-4-methyl-3-phenylmethylpyrido-[4,3-d]pyrimidine dihydrochloride | | | | −55% |

*difference in edema vs. control

The compounds of Formula I of the present invention are useful as analgesic agents due to their ability to alleviate pain in mammals. The activity of the compound is demonstrated in the 2-phenyl-1,4-benzoquinone-induced writhing test in mice, a standard assay for analgesia [Proc. Soc. Exptl. Biol. Med., 95, 729 (1957)]. Table 2 shows results of the test for some of the compounds of this invention along with a result for a reference compound.

TABLE 2

| | ANALGESIC ACTIVITY | |
|---|---|---|
| Compound | PQW % Inhibition of writhing | Dose (mg/kg, s.c.) |
| α-methyl-α-[4-(2,2-dimethylpropionamido)-3-pyridinyl]-methanol | 89 | 20 |
| N-(3-acetyl-4-pyridinyl)-2,2-dimethylpropanamide | 34 | 20 |
| 3-(butylamino)methyl-4-pyridinamine dihydrochloride | 62 | 20 |
| 4-amino-α-methyl-N-(phenylmethyl)-3- | 58 | 20 |

TABLE 2-continued

ANALGESIC ACTIVITY

| Compound | PQW % Inhibition of writhing | Dose (mg/kg. s.c.) |
|---|---|---|
| pyridinemethanamine 3-[(phenylmethyl-amino)methyl]-4-pyridinamine dihydrochloride | 40 | 20 |
| α-cyclohexyl-α-[4-(2,2-dimethyl-propionamideo)-3-pyridinyl]-methanol | 32 | 20 |
| 3,4-dihydro-4-methyl-3-phenylmethylpyrido-[4,3-d]pyrimidine dihydrochloride (Reference Compound) | 85 | 20 |
| Propoxyphene | 50 | 3.9 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include;

4-cyclohexyl-1,4-dihydropyrido[4,3-d]pyrimidine;
3,4-dihydro-4-methyl-3-phenylmethylpyrido[4,3-d]pyrimidine;
3-butyl-3,4-dihydropyrido[4,3-d]pyrimidine;
1,4-dihydro-4-phenylpyrido[4,3-d]pyrimidine;
1,4-dihydro-2,4-dimethylpyrido[4,3-d]pyrimidine;
1,4-dihydro-4-methyl-2-phenylmethylpyrido[4,3-d]pyrimidine; and
1,4-dihydro-4-methyl-2-phenylpyrido[4,3-d]pyrimidine.

The following examples are presented in order to illustrate this invention:

EXAMPLE 1

N-[3-[(Butylamino)methyl]-4-pyridinyl]-2,2-dimethyl-propanamide dihydrochloride

A solution of N-(3-formyl-4-pyridinyl)-2,2-dimethyl-propanamide[1] (10 g), n-butylamine (7.1 g) and p-toluenesulfonic acid monohydrate (0.1 g) in 150 ml toluene was stirred at reflux with removal of water. After six hours the solution was cooled and concentrated and the product purified by flash chromatography (silica, 50% ethyl acetate in dichloromethane) to yield 8 g oil. A solution of the imine (combined with 3 g obtained from another condensation) in 100 ml isopropanol and 25 ml methanol was stirred for one hour at 80° with sodium borohydride (5 g) and thereafter cooled, stirred with water and extracted with ether. The organic extract was washed with water and saturated sodium chloride solution, dried (anhy. MgSO$_4$), filtered and concentrated to an oil. This oil was purified by flash chromatography (silica, 50% ethyl acetate in dichloromethane) to yield 6.5 g oil. This oil was purified by column chromatography (alumina, ether) to yield 6 g oil. An analytical sample was obtained by converting 2.5 g to the dihydrochloride salt in methanol/ether to yield 2.7 g crystals, m.p. 166°–168°.

[1]Turner, J. Org. Chem., 48, 3401 (1983)

ANALYSIS: Calculated for C$_{15}$H$_{25}$N$_3$.2HCl: 53.57% C, 8.09% H, 12.50% N. Found: 53.58% C, 8.09% H, 12.53% N.

EXAMPLE 2

N-[3-[(Phenylmethylamino)methyl]-4-pyridinyl]-2,2-dimethylpropanamide dihydrochloride A solution of N-(3-formyl-4-pyridinyl)-2,2-dimethyl-propanamide (10 g), benzylamine (8 g) and p-toluenesulfonic acid monohydrate (0.1 g) in 125 ml toluene was stirred at reflux with removal of water. After two hours the solution was cooled and concentrated and the product purified by flash chromatography (silica, 20% ethyl acetate in dichloromethane) to yield 11.3 g solid, m.p. 105°–109°. A solution of the imine (11 g) in 100 ml isopropanol and 25 ml methanol was stirred for one hour at 80° C. with sodium borohydride (5 g) and thereafter cooled, stirred with water and extracted with ether. The organic extract was washed with water and saturated sodium chloride solution, dried (anhy. MgSO$_4$), filtered and concentrated to 12 g oil. This oil was purified by flash chromatography (silica, 50% ethyl acetate in dichloromethane) to yield 5.5 g oil*. An analytical sample was obtained by recrystallizing 3.2 g from ethanol/ether to yield 3.0 g crystals, m.p. 168°–170°.

*This oil was converted to the dihydrochloride salt in methanol/ether to yield 5.5 solid, m.p. 168°–170° C.

ANALYSIS: Calculated for $C_{18}H_{23}N_3O.2HCl$: 58.38% C, 6.80% H, 11.35% N. Found: 57.95% C, 6.83% H, 11.21% N.

EXAMPLE 3

α-Methyl-α-[4-(2,2-dimethylpropionamido)-3-pyridinyl]methanol

To an ice-cooled solution of N-(3-formyl-4-pyridinyl)-2,2-dimethylpropanamide[1] (8 g) in 150 ml tetrahydrofuran was added methylmagnesium bromide (3.0M in ether, 30 ml). After thirty minutes the reaction mixture was stirred with saturated ammonium chloride solution, basified with sodium carbonate and extracted with ether. The organic extract was washed with water and saturated sodium chloride solution, dried over anhydrous magnesium sulfate, filtered and concentrated to an oil. This oil was purified by flash chromatography (silica, ethyl acetate) to give 7 g oil. This oil was crystallized from ether/hexane to give 4.5 g solid, m.p. 100°–102°.

[1]Turner, J. Org. Chem., 48, 3401–3408 (1983)

ANALYSIS: Calculated for $C_{12}H_{18}N_2O_2$: 64.84% C, 8.16% H, 12.61% N. Found: 64.82% C, 8.23% H, 12.58% N.

EXAMPLE 4

N-(3-Acetyl-4-pyridinyl)-2,2-dimethylpropanamide

A solution of α-methyl-α-[4-(2,2-dimethylpropionamido)-3-pyridinyl]-methanol (11 g) and pyridinium dichromate (26 g) in 100 ml dimethylformamide was stirred at ambient temperature for twenty hours and thereafter stirred with water, basified with sodium carbonate and extracted with ether. The organic extract was washed with water and saturated sodium chloride solution, dried (anhy.MgSO$_4$), filtered and concentrated to 11 g waxy solid. This solid was purified by flash chromatography (silica, 20% ethyl acetate in dichloromethane) to yield 7 g solid, m.p. 95°. Six grams were recrystallized from hexane to yield 4.8 g crystals, m.p. 98°–100°. An analytical sample was obtained by recrystallizing 3 g from hexane to yield 2.7 g, m.p. 98°–100°.

ANALYSIS: Calculated for $C_{12}H_{16}N_2O_2$: 65.43% C, 7.32% H, 12.72% N. Found: 65.67% C, 7.52% H, 12.53% N.

EXAMPLE 5

N-[3-[1-(Phenylmethylamino)ethyl]-4-pyridinyl]-2,2-dimethylpropionamide dihydrochloride A solution of N-(3-acetyl-4-pyridinyl)-2,2-dimethylpropanamide (8 g), benzylamine (12 g) and p-toluenesulfonic acid monohydrate (0.2 g) in 200 ml xylene was stirred at reflux with removal of water. After eighteen hours the solution was cooled and concentrated and the product purified by flash chromatography (silica, 50% ethyl acetate in dichloromethane) to yield 9.4 g solid, m.p. 112°–115°. A solution of the imine (9.4 g) in 100 ml isopropanol and 25 ml methanol was stirred for two hours at 80° with sodium borohydride (2.3 g) and thereafter cooled, stirred with water and extracted with ethyl acetate. The organic extract was washed with water and saturated sodium chloride solution, dried (anhy.MgSO$_4$), filtered and concentrated to 9 g oil. This oil was purified by flash chromatography (silica, 30% ethyl acetate in dichloromethane) to yield 6.3 g oil. A 2.3 g portion was converted to the dihydrochloride salt in methanol/ether to yield 2.3 g solid, m.p. 205°. This was recrystallized from methanol/ether to yield 2.2 g crystals, m.p. 207°–209°.

ANALYSIS: Calculated for $C_{19}H_{27}Cl_2N_3O$: 59.37% C, 7.08% H, 10.94% N. Found: 59.20% C, 6.92% H, 10.89% N.

EXAMPLE 6

3-(Butylamino)methyl-4-pyridinamine dihydrochloride

A solution of N-[3-[(butylamino)methyl]-4-pyridinyl]-2,2-dimethylpropanamide (7 g) in 150 ml methanol and 15 ml 10% aqueous sodium hydroxide was stirred at reflux for 16 hours and thereafter concentrated, and the product was purified by flash chromatography (silica, 25% methanol in dichloromethane) to yield 4.5 g oil. This oil was converted to the dihydrochloride salt in methanol/ether to yield 3.7 g solid, m.p. 258°–260°.

ANALYSIS: Calculated for $C_{10}H_{17}N_3.2HCl$: 47.62% C, 7.59% H, 16.67% N. Found: 47.53% C, 7.50% H, 16.44% N.

EXAMPLE 7

4-Amino-α-methyl-N-(phenylmethyl)-3-pyridinemethanamine

A solution of N-[3-[1-(phenylmethylamino)ethyl]-4-pyridinyl]-2,2-dimethylpropanamide (12.2 g) in 200 ml n-propanol and 25 ml 10% aqueous sodium hydroxide was stirred at reflux for sixteen hours and thereafter cooled, stirred with water and extracted with ethyl acetate/ether. The organic extract was washed with water and saturated sodium chloride solution and thereafter dried (anhydrous magnesium sulfate), filtered and concentrated to 8.7 g oil. This oil was eluted with 20% methanol in dichloromethane through silica via flash column chromatography to yield 8 g oil. This oil was eluted with 10% methanol in dichloromethane through silica via HPLC to yield 7 g oil. Following unseccussful attempts to purify this oil as salts, the reconverted free base was again eluted with 20% methanol in dichloromethane through silica via HPLC to yield 5.5 g oil. A 3.5 g portion was converted to the dimaleate salt in methanol/ether to yield 4.5 g solid, d 78°–80°. This salt was reconverted to the free base to afford a solid which was recrystallized from 50% ether/hexane to yield 1.9 g crystals, m.p. 107°–109°.

ANALYSIS: Calculated for $C_{14}H_{17}N_3$: 73.97% C, 7.54% H, 18.49% N. Found: 74.17% C, 7.57% H, 18.40% N.

EXAMPLE 8

3-[(Phenylmethylamino)methyl]-4-pyridinamine dihydrochloride

A solution of N-[3-[(phenylmethylamino)methyl]-4-pyridinyl]-2,2-dimethylpropanamide (8 g) in 200 ml methanol and 20 ml 10% aqueous sodium hydroxide was stirred at reflux for 12 hours and thereafter cooled, stirred with water and extracted with ethyl acetate. The organic extract was washed with water and saturated sodium chloride solution and thereafter dried (anhy. MgSO$_4$), filtered and concentrated to 7 g oil. This oil was purified by flash chromatography (silica, 25% methanol in dichloromethane) to give 3.2 g oil. This oil was converted to the dihydrochloride salt in methanol to yield 2.5 g crystals, d 305°–307°.

ANALYSIS: Calculated for $C_{13}H_{17}Cl_2N_3$: 54.56% C, 5.99% H, 14.68% N. Found: 54.56% C, 5.88% H, 14.60% N.

EXAMPLE 9

α-Cyclohexyl-α-[4-(2,2-dimethylpropionamido)-3-pyridinyl]-methanol

To an ice-cooled solution of N-(3-formyl-4-pyridinyl)-2,2-dimethylpropanamide (10 g) in 100 ml tetrahydrofuran was added cyclohexylmagnesium chloride (2.0M in ether, 35 ml). After thirty minutes the reaction mixture was stirred with saturated ammonium chloride solution, basified with sodium carbonate and extracted with ether. The organic extract was washed with water and saturated sodium chloride solution, dried over anhydrous magnesium sulfate, filtered and concentrated to an oil. This oil was purified by flash chromatography (silica, 20% ethyl acetate in dichloromethane then ethyl acetate) to give 6 g oil. This oil was crystallized from hexane to give 2.5 g solid, m.p. 148°–150°. This solid was recrystallized from acetonitrile to give 2.1 g crystals, m.p. 153°–155°.

ANALYSIS: Calculated for $C_{17}H_{26}N_2O_2$: 70.31% C, 9.02% H, 9.65% N. Found: 70.11% C, 9.08% H, 9.65% N.

EXAMPLE 10

N-[3-(Cyclohexylcarbonyl)-4-pyridinyl]-2,2-dimethylpropanamide hydrochloride Pyridinium dichromate (30 g) was added to a solution of α-cyclohexyl-α-[4-(2,2-dimethylpropionamido)-3-pyridinyl]-methanol (16 g) and the resultant solution stirred 16 hours at ambient temperature and thereafter stirred with water, basified with sodium carbonate and extracted with ethyl acetate-ether. The organic extract was washed with water and saturated sodium chloride solution, dried(anhy. MgSO$_4$), filtered and concentrated to 12 g waxy solid. This was purified by flash chromatography (silica, 10% ethyl acetate in dichloromethane) to yield 11 g solid. This was purified by column chromatography (alumina, ether) to yield 9 g solid, m.p. 80°. Three grams were converted to the hydrochloride salt in ether to yield 3 g solid, m.p. 212°–215°. This was recrystallized from methanol/ether (1:40) to yield 2.2 g crystals, m.p. 216°–218°.

ANALYSIS: Calculated for $C_{17}H_{25}ClN_2O_2$: 62.85% C, 7.76% H, 8.63% N. Found: 63.25% C, 7.67% H, 8.61% N.

EXAMPLE 11

(4-Amino-3-pyridinyl)cyclohexylmethanone hydrochloride

A solution of N-[3-(cyclohexylcarbonyl)-4-pyridinyl]-2,2-dimethylpropanamide (5.5 g) in 100 ml methanol and 10 ml 10% aqueous sodium hydroxide was stirred for three hours at ambient temperature and thereafter concentrated, stirred with water and extracted with ethyl acetate. The organic extract was washed with water and saturated sodium chloride solution, dried (anhy. MgSO$_4$), filtered and concentrated to 5 g oil. This oil was purified by flash chromatography (silica, ethyl acetate) to yield 4 g viscous oil. This was converted to the hydrochloride salt in methanol/ether to yield 4.2 g crystals, dec. 266°–270°.

ANALYSIS: Calculated for $C_{12}H_{17}ClN_2O$: 59.87% C, 7.12% H, 11.64% N. Found: 59.80% C, 7.07% H, 11.56% N.

EXAMPLE 12

(4-Amino-3-pyridinyl)cyclohexylmethanone oxime hydrochloride

A solution of (4-amino-3-pyridinyl)cyclohexylmethanone (5 g) and hydroxylamine hydrochloride (10 g) in 70 ml pyridine was stirred at 80° C. for three hours and thereafter concentrated. The residue was stirred with water, basified with sodium carbonate and extracted with dichloromethane. The organic extract was washed with water and saturated sodium chloride solution. The dried (anhy. MgSO$_4$) organic layer was concentrated to 9 g waxy solid. This solid was triturated with acetonitrile to yield 4.9 g solid, m.p. 155°–158° C. Three grams were converted to the hydrochloride salt in methanol/ether to yield 2.8 g solid, m.p. 226°–228° C.

ANALYSIS: Calculated for $C_{12}H_{18}ClN_3O$: 56.35% C, 7.09% H, 16.43% N. Found: 56.30% C, 7.17% H, 16.07% N.

EXAMPLE 13

(4-Amino-3-pyridinyl)cyclohexylmethanamine dihydrochloride

A solution of (4-amino-3-pyridinyl)cyclohexylmethanone oxime (6 g) in 145 ml 95% ethanol was quickly treated with Raney alloy (10.7 g, 50:50 Al/Ni alloy) and then with a solution of sodium hydroxide (11.4 g) in 145 ml water. The exothermic reaction was controlled with a reflux condenser. The mixture was cooled to ambient temperature and stirred for four hours. The Raney nickel catalyst (pyrophoric) was removed by filtration and washed with 50% aqueous ethanol. The filtrate was concentrated by removing the ethanol and the aqueous residue was extracted with dichloromethane. The dried (anhy. MgSO$_4$) organic layer was concentrated to yield 5 g oil. This was combined with 0.6 g product obtained from a trial reduction and eluted with 20% methanol in dichloromethane through silica via flash column chromatography to yield 5.0 g oil. This oil was converted to the dihydrochloride salt in methanol and thereafter the methanol was removed by evaporation. The residue was recrystallized from 50% methanol in acetonitrile to yield 4.2 g crystals, d 314°–316°.

ANALYSIS: Calculated for $C_{12}H_{21}Cl_2N_3$: 51.80% C, 7.61% H, 15.11% N. Found: 51.78% c, 7.45% H, 15.03% N.

EXAMPLE 14

(4-Amino-3-pyridinyl)phenylmethanone oxime hydrochloride

A solution of (4-amino-3-pyridinyl)phenylmethanone (17 g prepared from N-(3-formyl-4-pyridinyl)-2,2-dimethylpropanamide by utilizing the reaction scheme described in Example 9, 10 and 11 except that phenyl magnesium chloride was used instead of cyclohexyl magnesium chloride) and hydroxylamine hydrochloride (24 g) in 150 ml pyridine was stirred at 90°–95° for two hours and thereafter cooled and concentrated. The residue was stirred with water, basified with sodium carbonate and extracted with dichloromethane. The dried organic layer was concentrated to 20 g waxy solid. This was triturated with acetonitrile to yield 13.6 g solid, m.p. 177°–179°. The filtrate was concentrated to 4.3 g oil and thereafter eluted with 10% methanol in dichloromethane through silica via flash column chromatography to yield an additional 1.8 g product for a total yield of 15.4 g. Eight grams were again eluted with 10% methanol in dichloromethane through silica via flash column chromatography to yield 6.9 g solid, m.p. 178°–180°. A 4.9 g portion was converted to the hydrochloride salt in methanol/ether to yield 3.3 g crystals, d 238°–240°.

ANALYSIS: Calculated for $C_{12}H_{12}ClN_3O$: 57.72% C, 4.84% H, 16.83% N. Found: 57.72% C, 4.69% H, 16.76% N.

EXAMPLE 15

(4-Amino-3-pyridinyl)benzenemethanamine dihydrochloride

A solution of (4-amino-3-pyridinyl)phenylmethanone oxime (6 g) in 147 ml 95% ethanol was quickly treated with Raney alloy (11 g, 50:50 Al/Ni alloy) and then with a solution of sodium hydroxide (11.7 g) in 147 ml water. The exothermic reaction was controlled with a reflux condenser. The mixture was cooled to ambient temperature and stirred for four hours. The Raney nickel catalyst (pyrophoric) was removed by filtration and washed with 50% aqueous ethanol. The filtrate was concentrated by removing the ethanol and the aqueous residue was extracted with dichloromethane. The dried (anhy. MgSO4) organic layer was concentrated to yield 5 g waxy solid. This solid was eluted with 20% methanol in dichloromethane through silica via flash column chromatography to yield 4.2 g solid, m.p. 108°–110°. This solid was converted to the dihydrochloride salt in methanol and thereafter the methanol was removed by evaporation. The solid residue was recrystallized from 50% methanol in acetonitrile to yield 3.7 g crystals, d 280°–282°.

ANALYSIS: Calculated for $C_{12}H_{15}Cl_2N_3$: 52.95% C, 5.56% H, 15.44% N. Found: 52.94% C, 5.47% H, 15.35% N.

EXAMPLE 16

4-Cyclohexyl-1,4-dihydropyrido[4,3-d]pyrimidine dihydrochloride

A solution of (4-amino-3-pyridinyl)cyclohexylmethanamine (4.7 g) in 30 ml triethyl orthoformate and 10 ml glacial acetic acid was stirred for one hour at 100° and thereafter cooled and concentrated. The residue was stirred with water and basified with sodium carbonate. The product was extracted with dichloromethane. The dried (anhydrous magnesium sulfate) organic layer was concentrated to 6 g oil. This oil was eluted through silica first with 5% methanol in dichloromethane and then with 10% methanol in dichloromethane via flash column chromatography to yield 4.6 g viscous oil. This oil was converted to the dihydrochloride salt in methanol with ethereal hydrogen chloride to yield 4 g crystals, d 260°–262°.

ANALYSIS: Calculated for $C_{13}H_{19}Cl_2N_3$: 54.17% C, 6.64% H, 14.58% N. Found: 53.76% C, 6.60% H, 14.39% N.

EXAMPLE 17

3,4-Dihydro-4-methyl-3-phenylmethylpyrido[4,3-d]pyrimidine dihydrochloride

A solution of 4-amino-α-methyl-N-(phenylmethyl)-3-pyridinemethanamine (3 g) in triethyl orthoformate (25 ml) and glacial acetic acid (8 ml) was stirred at 100°–105° for one hour and thereafter cooled and concentrated. The residue was stirred with water, basified with sodium carbonate and extracted with dichloromethane. The dried (anhydrous magnesium sulfate) organic layer was filtered and concentrated to 2.4 g oil. This oil was eluted through silica first with ethyl acetate and then with 10% methanol in ethyl acetate via flash column chromatography to give 2.1 g oil. This oil was converted to the dihydrochloride salt in methanol/ether to give 2.1 g solid. This was recrystallized from methanol/ether to yield 1.8 g crystals, d 244°–246°.

ANALYSIS: Calculated for $C_{15}H_{17}Cl_2N_3$: 58.07% C, 5.52% H, 13.55% N. Found: 57.78% C, 5.68% H, 13.35% N.

We claim:

1. A method of treating a patient in need of relief from pain which comprises administering to such a patient an effective amount of a compound having the formula

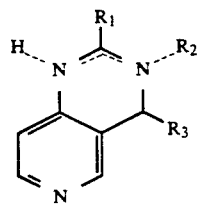

where
- $R_1$ is hydrogen, loweralkyl, arylloweralkyl or aryl;
- $R_2$ when present is hydrogen, loweralkyl, aryllower-alkyl; and
- $R_3$ is hydrogen, loweralkyl, $C_3$-$C_6$ cycloalkyl or aryl.

2. A method of treating a patient in need of relief from pain which comprises administering to such a patient an effective amount of a compound having the formula

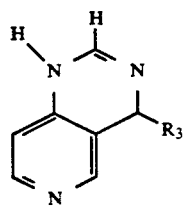

where $R_3$ is hydrogen, loweralkyl, $C_3$-$C_6$ cycloalkyl or aryl.
3. A method of treating a patient in need of relief from pain which comprises administering to such a patient an effective amount of a compound having the formula
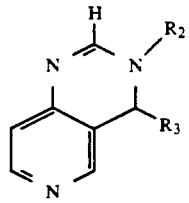
where $R_2$ is hydrogen, loweralkyl, arylloweralkyl; and $R_3$ is hydrogen, loweralkyl, $C_3$-$C_6$ cycloalkyl or aryl.
* * * * *